United States Patent
Owens et al.

(10) Patent No.: US 10,463,589 B2
(45) Date of Patent: *Nov. 5, 2019

(54) HAIR DYE COMPOSITION

(71) Applicant: KAO CORPORATION, Tokyo (JP)

(72) Inventors: Chris Owens, Fort Thomas, KY (US); Takashi Kanda, Ichikawa (JP); Masayoshi Nojiri, Chiba (JP)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/775,556

(22) PCT Filed: Nov. 9, 2016

(86) PCT No.: PCT/JP2016/083165
§ 371 (c)(1),
(2) Date: May 11, 2018

(87) PCT Pub. No.: WO2017/082267
PCT Pub. Date: May 18, 2017

(65) Prior Publication Data
US 2018/0369103 A1    Dec. 27, 2018

Related U.S. Application Data

(60) Provisional application No. 62/254,912, filed on Nov. 13, 2015, provisional application No. 62/382,540, filed on Sep. 1, 2016.

(51) Int. Cl.
| | | |
|---|---|---|
| A61Q 5/10 | (2006.01) | |
| A61K 8/49 | (2006.01) | |
| A61K 8/73 | (2006.01) | |
| A61K 8/81 | (2006.01) | |
| A61K 8/40 | (2006.01) | |

(52) U.S. Cl.
CPC ............. *A61K 8/49* (2013.01); *A61K 8/40* (2013.01); *A61K 8/4946* (2013.01); *A61K 8/731* (2013.01); *A61K 8/817* (2013.01); *A61K 8/8182* (2013.01); *A61Q 5/10* (2013.01); *A61K 2800/4324* (2013.01)

(58) Field of Classification Search
CPC . A61Q 5/10; A61K 8/49; A61K 8/731; A61K 8/817
See application file for complete search history.

(56) References Cited

U.S. PATENT DOCUMENTS

| | | | |
|---|---|---|---|
| 2004/0019982 A1* | 2/2004 | Pratt | A61K 8/466 8/405 |
| 2006/0064823 A1 | 3/2006 | Marsh et al. | |
| 2009/0049622 A1 | 2/2009 | Matsunaga et al. | |
| 2010/0125956 A1* | 5/2010 | Koike | A61K 8/23 8/429 |
| 2014/0366907 A1 | 12/2014 | Fack et al. | |
| 2015/0328100 A1 | 11/2015 | Möhring et al. | |
| 2016/0120783 A1* | 5/2016 | Horie | A61Q 5/12 424/62 |
| 2017/0196790 A1 | 7/2017 | Saimiya et al. | |

FOREIGN PATENT DOCUMENTS

| | | | |
|---|---|---|---|
| EP | 2 883 530 A1 | 6/2015 | |
| EP | 2 883 531 A1 | 6/2015 | |
| JP | 2003-342139 A | 12/2003 | |
| JP | 2006-213663 A | 8/2006 | |
| JP | 2007-326818 A | 12/2007 | |
| JP | 2010-24158 A | 2/2010 | |
| JP | 2010024158 A * | 2/2010 | ............... A61Q 5/10 |
| JP | 2013-56950 A | 3/2013 | |
| JP | 2015-13854 A | 1/2015 | |
| JP | 2015-13855 A | 1/2015 | |
| WO | WO 2013/092562 A1 | 6/2013 | |
| WO | WO 2013/092904 A2 | 6/2013 | |
| WO | WO 2014/196579 A1 | 12/2014 | |
| WO | WO 2014196579 A1 * | 12/2014 | ............... A61Q 5/12 |
| WO | WO 2015/186815 A1 | 12/2015 | |

OTHER PUBLICATIONS

English transalation of the Japanese Patent No. JP 2010-024158 (Apr. 2010).*
International Search Report dated Jan. 10, 2017 in PCT/JP2016/083165 filed Nov. 9, 2016.
Supplementary European Search Report dated Jun. 17, 2019 issued in corresponding European patent application No. 16864228.8.

* cited by examiner

*Primary Examiner* — Eisa B Elhilo

(74) *Attorney, Agent, or Firm* — Oblon, McClelland, Maier & Neustadt, L.L.P.

(57) ABSTRACT

A hair dye composition containing components (A) to (C), and having a mass ratio of component (B) to component (C), (B)/(C), of 0.1 to 30, and a pH (25° C.) of 8.5 to 12. (A): a dye selected from (A-1), (A-2) and (A-3). (B): a cationic polymer having a charge density of 3.0 meq/g or higher. (C): an anionic polysaccharide derivative where part of hydrogen atoms of hydroxy groups of a polysaccharide compound having a constitutional unit of formula (1) is substituted by —$(CH_2)_m COO^-$ (m is an integer of 1 to 5); an average degree of substitution per the constitutional unit thereby is 0.5 to 2.0; and part of hydrogen atoms of remaining hydroxy groups is optionally substituted by a $C_{1-40}$ alkyl group and/or alkylene group, where R is a $C_{2-4}$ alkylene group, and n is the number that makes an average addition molar number of RO per the constitutional unit 0 to 10.

19 Claims, No Drawings

HAIR DYE COMPOSITION

FIELD OF THE INVENTION

The present invention relates to a hair dye composition.

BACKGROUND OF THE INVENTION

Hair dye compositions are classified depending upon the types of dyes to be used or the presence or absence of a melanin bleaching action. Typical examples of the hair dye compositions include a two-agent type oxidative hair dye composition consisting of a first agent containing an alkali agent, an oxidation dye and an optional direct dye such as a nitro dye and a second agent containing an oxidizing agent; and one-agent type non-oxidative hair dye composition containing a pH adjuster (acid or alkali) and at least one of direct dye such as an acid dye, a basic dye and a nitro dye.

Patent Document 1 mentions that the incorporation of a specific cationic polymer having a high charge density and a specific anionic polysaccharide derivative having a low viscosity in these hair dyes and a hair cosmetic such as a shampoo, a hair treatment or a styling agent can attain high improving effect on finger combability and combability after treatment with the hair cosmetic.

Patent Document 2 discloses a technology of improving hair dyeability by combining a cationic polymer and a specific salt in a hair dye composition containing a specific azo dye, and it describes an anionic polymer as a water-soluble polymer which can be used.

(Patent Document 1) WO2014/196579
(Patent Document 2) WO2015/186815

SUMMARY OF INVENTION

The present invention provides a hair dye composition comprising the following components (A) to (C), and having a mass ratio of the component (B) to the component (C), (B)/(C), of 0.1 or higher and 30 or lower and a pH (25° C.) of from 8.5 to 12.

(A) one or more dyes selected from the group consisting of the following (A-1), (A-2) and (A-3).

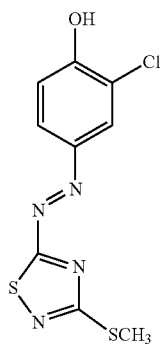
(A-1)

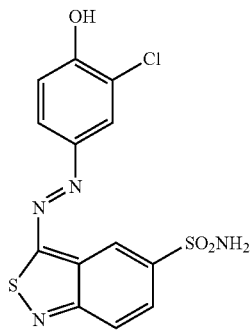
(A-2)

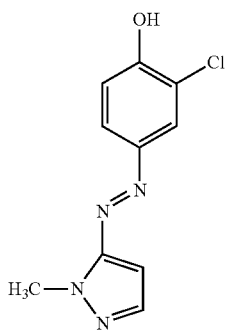
(A-3)

(B) a cationic polymer having a charge density of 3.0 meq/g or higher.

(C) an anionic polysaccharide derivative in which part of hydrogen atoms of hydroxy groups of a polysaccharide compound having a constitutional unit represented by the formula (1) is substituted by a group —$(CH_2)_m COO^-$ (m is an integer of from 1 to 5); the average degree of substitution per the constitutional unit by the group is 0.5 or higher and 2.0 or lower; and part of hydrogen atoms of the remaining hydroxy groups is optionally substituted by a straight-chain or branched-chain alkyl group and/or alkylene group having 1 to 40 carbon atoms.

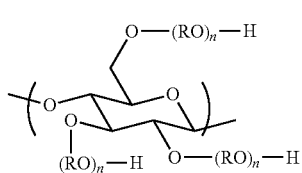
(1)

In the formula, each R may be identical or different and denotes a straight-chain or branched-chain alkylene group having 2 to 4 carbon atoms which is optionally substituted with a hydroxy group(s); and n denotes a number that makes an average addition molar number of RO per the constitutional unit of 0 to 10.

The present invention further provides a hair bleaching or dyeing method comprising a step of applying the above hair dye composition on the hair, a step of leaving the composition for from 1 to 60 minutes, and a step of rinsing the composition off by using water.

DETAILED DESCRIPTION OF INVENTION

Since dyeing unevenness occurs when a hair dye composition cannot be applied and spread uniformly on the hair, a hair dye composition is desired to be easily applied and spread on the hair. As one of the means for solving, it is conceivable that the hair is wetted with water in advance. Since wet hair has swellability differing depending on the chemical treatment history of the hair and the distance from their roots, however, problems of dyeing unevenness can occur due to causes other than the above.

The present invention relates to a hair dye composition which is easily applied and spread regardless of whether the hair on which the composition is to be applied is wet or dry, exhibits no dyeing unevenness because a direct dye fully penetrates the hair, and simultaneously dyes firmly the hair.

The present inventors have found that incorporation of a specific dye, and a specific cationic polymer and a specific anionic polysaccharide derivative in a hair dye composition having a pH in a specific range can solve the above problems all together.

In the present description, a first part refers to a composition containing an alkali agent; a second part refers to a composition containing hydrogen peroxide; and a third part refers to a composition containing effective components other than the alkali agent and the hydrogen peroxide. Further a hair dye composition, for a two-part type or a three-part type, refers to a mixture of each part. Further with respect to each component, the content thereof "in a hair dye composition" refers to a content thereof "in the hair dye composition" for a one-part type; a content thereof "in a mixture of the first part and the second part" for a two-part type; and a content thereof "in a mixture composed of the first to third parts" for a three-part type.

<Component (A): Dyes>

The hair dye composition of the present invention comprises one or more dyes selected from the group consisting of the following (A-1), (A-2) and (A-3).

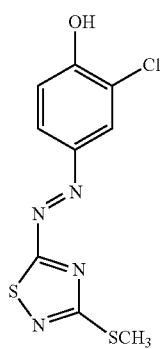

(A-1)

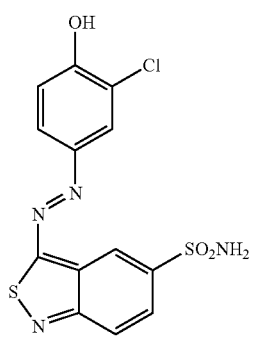

(A-2)

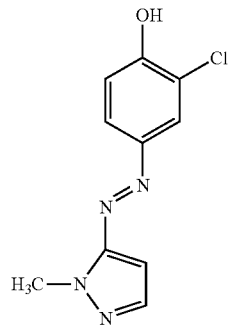

(A-3)

Here, the pKa of the dyes (A-1), (A-2) and (A-3) are 6.0, 6.0 and 7.5, respectively. Therefore, in the hair dye composition of the present invention having a pH (25° C.) of 8.5 to 12, 80% or more of these dyes is present in a proton-dissociated anionic state. When protons are dissociated, (A-1) assumes red; (A-2) assumes blue; and (A-3) assumes yellow.

The content of the component (A) in the hair dye composition is preferably 0.0005 mass % or higher, more preferably 0.001 mass % or higher, and still more preferably 0.01 mass % or higher from the viewpoint of excellent hair dyeability, and preferably 5 mass % or lower, more preferably 3 mass % or lower, still more preferably 2.5 mass % or lower, further still more preferably 1.5 mass % or lower, and further still more preferably 1 mass % or lower from the viewpoint of the stability of formulation and blending. Further the hair dye composition of the present invention, though having excellent hair dyeability without concurrent use of dyes other than the component (A), can also concurrently further use dyes other than the component (A) for correction of the hair dyeing color tone provided by the component (A). In this case, from the viewpoint that the dyes other than the component (A) are for color tone correction as described above, the proportion of the component (A) in the whole dye is preferably 1 mass % or higher, more preferably 5 mass % or higher, still more preferably 10 mass % or higher, further still more preferably 20 mass % or higher, further still more preferably 30 mass % or higher, and further still more preferably 40 mass % or higher.

[Oxidation Dye]

When the hair dye composition of the present invention is a two-part type or a three-part type, the first part can also comprise an oxidation dye in addition to the dye of the component (A). As a suitable oxidation dye for the hair dye composition of the present invention, well-known precursors and couplers used for usual hair dyes can be used.

Examples of the precursors include para-phenylenediamine, toluene-2,5-diamine, 2-chloro-para-phenylenediamine, para-aminophenol, para-methylaminophenol, ortho-aminophenol, 2,4-diaminophenol, N-phenyl-para-phenylenediamine, and salts thereof.

Examples of the couplers include meta-phenylenediamine, 2,4-diaminophenoxyethanol, meta-aminophenol, 2-methyl-5-aminophenol, 2-methyl-5-(2-hydroxyethylamino)phenol, resorcinol, 1-naphthol, 1,5-dihydroxynaphthalene, hydroquinone, and salts thereof.

The precursors and the couplers each may be used singly or in combination of two or more. The total content thereof in the hair dye composition is preferably 0.01 mass % or higher, and more preferably 0.1 mass % or higher from the viewpoint of correcting the color tone of the above dyes (A-1), (A-2) and (A-3), and preferably 5 mass % or lower, more preferably 3 mass % or lower, still more preferably 2 mass % or lower, further still more preferably 1.0 mass % or lower, and further still more preferably 0.5 mass % or lower from the viewpoint of not affecting the dyeability of the above dyes (A-1), (A-2) and (A-3).

[Direct Dyes Other than the Component (A)]

The hair dye composition of the present invention can further comprise a direct dye other than the above dyes (A-1), (A-2) and (A-3). As the direct dye, there can be used well-known dyes utilizable for hair dyes, such as acid dyes, basic dyes, nitro dyes and disperse dyes.

Examples of the acid dyes include Blue No. 1, Violet No. 401, Black No. 401, Orange No. 205, Red No. 227, Red No. 106, Yellow No. 203 and Acid Orange 3. Examples of the basic dyes include Basic Blue 99, Basic Brown 16, Basic Brown 17, Basic Red 76 and Basic Yellow 57.

Examples of direct dyes other than the acid dyes and the basic dyes include 2-nitro-p-phenylenediamine, 2-amino-6-chloro-4-nitrophenol, 3-nitro-p-hydroxyethylaminophenol, 4-nitro-o-phenylenediamine, 4-amino-3-nitrophenol, 4-hydroxypropylamino-3-nitrophenol, N,N-bis(2-hydroxyethyl)-2-nitro-p-phenylenediamine, Disperse Violet 1, Disperse Blue 1, Disperse Black 9, HC Blue 2, HC Orange 1, HC Red 1, HC Red 3, HC Yellow 2, HC Yellow 4 and HC Yellow 5.

These direct dyes other than the dyes (A-1), (A-2) and (A-3) can be used singly or in combination of two or more, and the content thereof in the hair dye composition is preferably 0.001 mass % or higher, and more preferably 0.01 mass % or higher from the viewpoint of excellent dyeability, and preferably 5 mass % or lower, more preferably 3 mass % or lower, still more preferably 2 mass % or lower, further still more preferably 1.0 mass % or lower, and further still more preferably 0.5 mass % or lower from the viewpoint of the formulation stability.

<Component (B): A Cationic Polymer Having a Charge Density of 3.0 Meq/g or Higher>

The hair dye composition of the present invention comprises a cationic polymer having a charge density of 3.0 meq/g or higher. Here, the charge density of the cationic polymer refers to a cationic group molar number×1,000 per 1 g of the polymer (meq/g).

The charge density of the component (B) is preferably 3.5 meq/g or higher, more preferably 4.0 meq/g or higher, and still more preferably 4.5 meq/g or higher from the viewpoint of exhibiting high hair dyeability on healthy hair and damaged hair as well and also dry hair and wet hair as well, and preferably 7.0 meq/g or lower, and more preferably 6.5 meq/g or lower from the viewpoint of providing excellent feel.

The component (B) includes a polymer comprising a diallyl quaternary ammonium salt as a constitutional unit and a quaternized polyvinylimidazolium derivative.

The polymer comprising a diallyl quaternary ammonium salt as a constitutional unit is, from the viewpoint of exhibiting high hair dyeability on healthy hair and damaged hair as well and also dry hair and wet hair as well, and from the viewpoint of providing excellent feel, preferably one having a skeleton represented by the following formula (2) or (3).

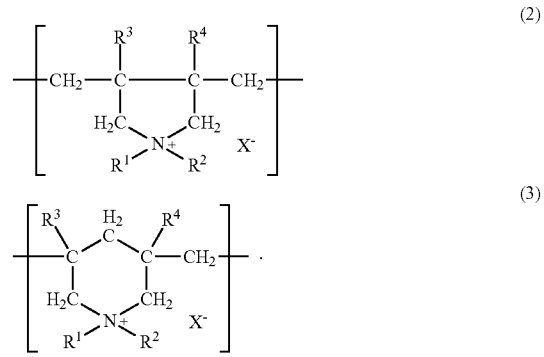

In the formula, $R^1$ and $R^2$ may be identical or different, and each denotes a hydrogen atom, an alkyl group having 1 to 18 carbon atoms, an aryl group (phenyl group or the like), a hydroxyalkyl group, an amidoalkyl group, a cyanoalkyl group, an alkoxyalkyl group or a carboalkoxyalkyl group; $R^3$ and $R^4$ may be identical or different, and each denotes a hydrogen atom, an alkyl group having 1 to 3 carbon atoms, or a phenyl group; and $X^-$ denotes an anion (chloride ion, bromide ion, iodide ion, sulfate anion, sulfonate anion, methylsulfate anion, phosphate anion, nitrate anion or the like).

The polymer of a diallyl quaternary ammonium salt contains, from the viewpoint of exhibiting high hair dyeability on healthy hair and damaged hair as well and also dry hair and wet hair as well, the constitutional unit represented by the formula (2) or (3) of preferably 30 to 100 mol % in one molecule thereof, more preferably 45 to 100 mol %, still more preferably 50 to 100 mol %, further still more preferably 50 to 80 mol %, and further still more preferably 55 to 75 mol %.

Examples of the polymer comprising a diallyl quaternary ammonium salt as a constitutional unit include a polymer represented by the following formula (4) or (5).

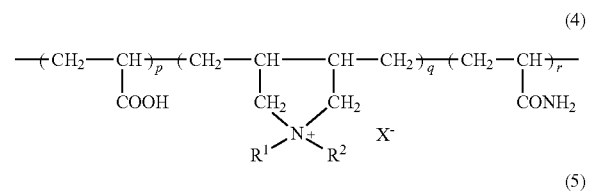

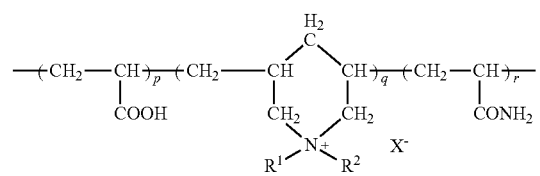

In the formula, $R^1$, $R^2$ and $X^-$ denote the same meaning as in the above; and p, q and r denote molar ratios, and p+q+r=100.

p is preferably 0 to 50, more preferably 10 to 45, and still more preferably 20 to 40 from the viewpoint of exhibiting high hair dyeability on healthy hair and damaged hair as well and also dry hair and wet hair as well, and simultaneously providing excellent feel on hair; q is preferably from 30 to 100, more preferably from 45 to 100, still more preferably from 50 to 100, further still more preferably from 50 to 80, and further still more preferably from 55 to 75 from the viewpoint of exhibiting high hair dyeability on healthy hair and damaged hair as well and also dry hair and wet hair as well, and simultaneously providing excellent feel on hair; and r is preferably from 0 to 50, more preferably from 0 to 25, still more preferably from 0 to 10, and further still more preferably from 0 to 5 from the viewpoint of excellent hair dyeability.

Among these, preferable are homopolymers of a diallyl quaternary ammonium salt and copolymers of a diallyl quaternary ammonium salt with acrylic acid. A specific example of the homopolymers of a diallyl quaternary ammonium salt includes Merquat 100 (manufactured by Lubrizol Advanced Materials, Inc., charge density: 6.2 meq/g, weight-average molecular weight: 150,000); and specific examples of the copolymers of a diallyl quaternary ammonium salt with acrylic acid include Merquat 295 (manufactured by Lubrizol Advanced Materials, Inc., charge density: 6.0 meq/g, weight-average molecular weight: 190,000) and Merquat 280 (manufactured by Lubrizol Advanced Materials, Inc., charge density: 5.0 meq/g, weight-average molecular weight: 450,000).

As the quaternized polyvinylimidazolium derivative, from the viewpoint of exhibiting high hair dyeability on healthy hair and damaged hair as well and also dry hair and wet hair as well, and from the viewpoint of providing excellent feel, preferable is a quaternized polyvinylimidazolium derivative represented, for example, by the following formula (6).

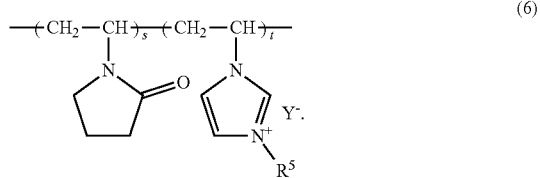

(6)

In the formula, $R^5$ denotes an alkyl group having 1 to 3 carbon atoms; $Y^-$ denotes an anion such as a chloride ion, a bromide ion, an iodide ion, a sulfate anion, a sulfonate anion, an alkylsulfate anion having 1 to 4 carbon atoms, a phosphate anion, or a nitrate anion; and s and t denote molar ratios, and s+t=100.

t, which is a molar ratio of a monomer exhibiting cationicity, is preferably from 73 to 99, more preferably 90 or higher, and still more preferably 93 or higher from the viewpoint of exhibiting high hair dyeability on healthy hair and damaged hair as well and also dry hair and wet hair as well.

Examples of the quaternized polyvinylimidazolium derivative include a copolymer of vinylpyrrolidone with methylvinylimidazolium chloride (Luviquat Excellence manufactured by BASF AG, charge density: 6.1 meq/g, weight-average molecular weight: 40,000).

The weight-average molecular weight of the component (B) is preferably 10,000 or higher, more preferably 50,000 or higher, and still more preferably 100,000 or higher from the viewpoint of exhibiting high hair dyeability on healthy hair and damaged hair as well and also dry hair and wet hair as well, and preferably 3,000,000 or lower, more preferably 1,000,000 or lower, and still more preferably 800,000 or lower from the viewpoint of providing excellent feel.

Here, the weight-average molecular weight can be measured, for example, by gel permeation chromatography (GPC) under the following conditions:

Mobile phase: 50 mM LiBr, 1% CH3COOH/ethanol:water 3:7

Columns: TSK gel α-M (two columns in series)

Standard material: polyethylene glycol

Among these components (B), homopolymers of a diallyl quaternary ammonium salt and copolymers of a diallyl quaternary ammonium salt with acrylic acid are preferable.

The component (B), for a two-part type or a three-part type, may be contained in any of the first part, the second part and the third part.

The content of the component (B) in the hair dye composition is preferably 0.01 mass % or higher, more preferably 0.1 mass % or higher, still more preferably 0.5 mass % or higher, and further still more preferably 0.75 mass % or higher from the viewpoint of exhibiting high hair dyeability on healthy hair and damaged hair as well and also dry hair and wet hair as well, and preferably 20 mass % or lower, more preferably 10 mass % or lower, still more preferably 5 mass % or lower, and further still more preferably 3 mass % or lower from the viewpoint of providing excellent feel.

<Component (C): Anionic Polysaccharide Derivative>

The hair dye composition of the present invention comprises an anionic polysaccharide derivative in which part of hydrogen atoms of hydroxy groups of a polysaccharide compound having a constitutional unit represented by the formula (1) is substituted by a group —$(CH_2)_m COO^-$ (m is an integer of from 1 to 5); the average degree of substitution per the constitutional unit by the group is 0.5 or higher and 2.0 or lower (from 0.5 to 2.0); and part of hydrogen atoms of the remaining hydroxy groups is optionally substituted by a straight-chain or branched-chain alkyl group and/or alkylene group having 1 to 40 carbon atoms.

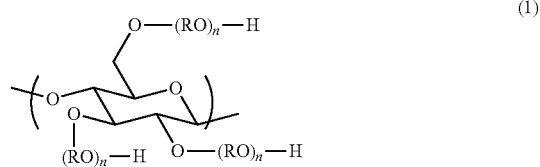

(1)

In the formula, each R may be identical or different and denotes a straight-chain or branched-chain alkylene group having 2 to 4 carbon atoms which is optionally substituted with a hydroxy group(s); and n denotes the number that makes an average addition molar number of RO per the constitutional unit 0 to 10.

In the component (C), m in the group —$(CH_2)_m COO^-$ is preferably an integer of from 1 to 3, more preferably from 1 or 2, and still more preferably 1 from the viewpoint of exhibiting high hair dyeability on healthy hair and damaged hair as well and also dry hair and wet hair as well. Further n in the formula (1) is preferably from 0 to 5, more preferably from 0 to 3, even more preferably from 0 or 1, and further more preferably 0 from the viewpoint of exhibiting high hair dyeability on healthy hair and damaged hair as well and also dry hair and wet hair as well. Further the number of carbon atoms of R is preferably from 2 or 3, and more preferably 2 from the viewpoint of exhibiting high hair dyeability on healthy hair and damaged hair as well and also dry hair and wet hair as well.

As the polysaccharide compounds having the constitutional unit represented by the above formula (1), at least one selected from the group consisting of cellulose, guar gum, starch, hydroxyethyl cellulose, hydroxyethyl guar gum, hydroxyethyl starch, methyl cellulose, methyl guar gum, methyl starch, ethyl cellulose, ethyl guar gum, ethyl starch, hydroxypropyl cellulose, hydroxypropyl guar gum, hydroxypropyl starch, hydroxyethyl methyl cellulose, hydroxyethyl methyl guar gum, hydroxyethyl methyl starch, hydroxypropyl methyl cellulose, hydroxypropyl methyl guar gum, and hydroxypropyl methyl starch can suitably be used. Among these, cellulose and hydroxyethyl cellulose can be used more suitably from the viewpoint of exhibiting high hair dyeability on healthy hair and damaged hair as well and also dry hair and wet hair as well and from the viewpoint of providing excellent feel.

Among the anionic polysaccharide derivative of the component (C), carboxymethyl cellulose is preferable from the viewpoint of exhibiting high hair dyeability on healthy hair and damaged hair as well and also dry hair and wet hair as well.

[Average Degree of Substitution]

In the component (C), the average degree of substitution per the constitutional unit by the group $-(CH_2)_mCOO^-$ is 0.5 or higher and 2.0 or lower (0.5-2.0), and preferably 0.6 or higher, and more preferably 0.65 or higher from the viewpoint of exhibiting high hair dyeability on healthy hair and damaged hair as well and also dry hair and wet hair as well, and preferably 1.5 or lower from the viewpoint of providing excellent feel.

Measurement Method of the Average Degree of Substitution

The method will be described by taking, for example, the case where an introduced substituent is $-(CH_2)_mCOONa$.

An absolutely dried anionic polysaccharide derivative is decomposed in wet with a sulfuric acid-hydrogen peroxide by using a microwave wet-type ashing apparatus (manufactured by Prolabo Co., trade name: "A-300"), and thereafter measured for the Na content (%) by an atomic absorption method using an atomic absorption apparatus (manufactured by Hitachi, Ltd., trade name: "Z-6100 type"); and the degree of substitution is calculated using the following calculation expression.

Average degree of substitution (DS)=($x$×a Na content (%))/(2,300−$y$×the Na content (%))

x: an average molecular weight per one unit of a sugar monomer constituting a polysaccharide derivative before introduction of an anionic substituent y: an increment of the molecular weight by the introduction of the one substituent.

[Viscosity of the Component (C)]

In the component (C), the viscosity of a 1 mass % aqueous solution thereof at 25° C. is preferably 120 mPa·s or higher, more preferably 150 mPa·s or higher, still more preferably 200 mPa·s or higher, further still more preferably 800 mPa·s or higher, further still more preferably 1,000 mPa·s or higher, and further still more preferably 1,500 mPa·s or higher from the viewpoint of applicability to the hair, and further, preferably 300,000 mPa·s or lower, more preferably 200,000 mPa·s or lower, still more preferably 150,000 mPa·s or lower, further still more preferably 100,000 mPa·s or lower, further still more preferably 80,000 mPa·s or lower, further still more preferably 50,000 mPa·s or lower, further still more preferably 20,000 mPa·s or lower, and further still more preferably 10,000 mPa·s or lower from the viewpoint of ease of blending. Here, in the present invention, the above viscosity of the component (C) is measured according to a method shown in the below.

Measurement Method of the Viscosity (mPa·s) of the 1 Mass % Aqueous Solution

About 2.2 g of a sample, whose moisture value is known, of an anionic polysaccharide derivative is precisely weighed in a 300 mL stoppered Erlenmeyer flask; 200 g of distilled water is added; immediately, the flask is stoppered and vigorously shaken to disperse the anionic polysaccharide derivative into small lumps, and left as it is. After the composition is left for one night (about 18 to 20 hours), the concentration of the anionic polysaccharide derivative in the aqueous solution is adjusted to 1 mass % by adding water for correction with the known moisture value being taken into consideration. The amount of the water for correction is calculated by the following calculation expression by using the separately determined moisture content.

Amount of water for correction (g) the sample of an anionic polysaccharide derivative (g)×(99−a moisture content (%) of the sample)−200

After the completion of the correction, a small stirrer bar is put in the Erlenmeyer flask and the resultant mixture is stirred by a magnetic stirrer for 25 minutes to completely disperse and dissolve the content in a swelling state. When the mixture has a high viscosity and cannot be dispersed and dissolved, the mixture is transferred to a 300 mL beaker, which is then sealed with a Parafilm (Bemis Flexible Packaging Co., Ltd.); and the mixture is stirred for 25 minutes by using a stirring blade to thereby completely disperse and dissolve the content. Then, the solution is transferred to a 250 mL stoppered vessel (50 mm in opening diameter×140 mm in height), which is then stoppered and left in a thermostatic chamber at 25° C. for 30 minutes. After the temperature of 25° C. is confirmed, a viscometer, a rotor and a guard are selectively attached to the stoppered vessel as follows, and the viscosity is measured. The measurement is carried out in the order of measurement conditions from low viscosity to high visdosity, and completed at the time point where the measurement can be carried out without over-ranging of the indication of the viscometer.

(When the Viscosity at 25° C. is 2,000 mPa·s or Lower)

When the viscosity at 25° C. is 2,000 mPa·s or lower, a Brookfield Viscometer (Model: LV DV-I Prime, manufactured by Brookfield Co.) is used and a value acquired after an LV Spindle(63) is rotated under the condition of a rotation frequency of 60 rpm at 25° C. for 3 minutes is taken as the viscosity.

(When the Viscosity at 25° C. is Higher than 2,000 mPa·s and 10,000 mPa·s or Lower)

When the viscosity at 25° C. is higher than 2,000 mPa·s and 10,000 mPa·s or lower, a Brookfield Viscometer (Model: LV DV-I Prime, manufactured by Brookfield Co.) is used and a value acquired after an LV Spindle(64) is rotated under the condition of a rotation frequency of 60 rpm at 25° C. for 3 minutes is taken as the viscosity.

(When the Viscosity at 25° C. is Higher than 10,000 mPa·s and 80,000 mPa·s or Lower)

When the viscosity at 25° C. is higher than 10,000 mPa·s and 80,000 mPa·s or lower, a Brookfield Viscometer (Model: RV DV-I Prime, manufactured by Brookfield Co.) with a helical stand is used and a value acquired after a Helipath Spindle (T-bar spindle E(95)) is rotated under the condition of a rotation frequency of 60 rpm at 25° C. for 3 minutes is taken as the viscosity.

(When the Viscosity at 25° C. is Higher than 80,000 mPa·s)

When the viscosity at 25° C. is higher than 80,000 mPa·s, a Brookfield Viscometer (Model: RV DV-I Prime, manufactured by Brookfield Co.) with a helical stand is used and a value acquired after a Helipath Spindle(T-bar spindle F(96)) is rotated under the condition of a rotation frequency of 60 rpm at 25° C. for 3 minutes is taken as the viscosity.

Specific examples of the component (C) include Cellogen F-5A, F-7A, F-907A, F-815A, F-SB, F-930A, F-3H, F-BSH-5, F-BSH-6, F-BSH-12, F-6HS9 and HE-1500F (manufactured by Dai-ichi Kogyo Seiyaku Co., Ltd., carboxymethyl cellulose), Sunrose F-01MC, FT-1, FO4HC, APP-84, F150LC, F120MC, F600MC, F350HC, F800HC and F1400MC (manufactured by Nippon Paper Industries Co., Ltd., carboxymethyl cellulose), CMC Daicel 1105, 1110, 1130, 1150, 1205, 1210, 1220, 1230, 1240, 1250, 1330, 1180, 1190, 1380, 1390, 2200, 2260 and 2280 (manufactured by Daicel Corp., carboxymethyl cellulose), and Blanose 7LF, 7M1F, 7MF, 7M8SF, 12M8P and 12M31XP (manufactured by Ashland, Inc., carboxymethyl cellulose).

From the viewpoint of the stability, the component (C) is contained preferably in the first part when the hair dye composition is a two-part type, and is contained preferably in the first part or the third part, more preferably in the third part when the hair dye composition is a three-part type.

The content of the component (C) in the hair dye composition is preferably 0.01 mass % or higher, more preferably 0.1 mass % or higher, still more preferably 0.3 mass % or higher, and further still more preferably 0.5 mass or higher from the viewpoint of exhibiting high hair dyeability on healthy hair and damaged hair as well and also dry hair and wet hair as well, and further, preferably 20 mass % or lower, more preferably 10 mass % or lower, still more preferably 5 mass % or less, further still more preferably 3 mass % or lower, further still more preferably 2.0 mass % or lower, and further still more preferably 1.5 mass % or lower from the viewpoint of ease of blending.

The mass ratio of the component (B) to the component (C), (B)/(C), in the hair dye composition of the present invention is preferably 0.1 or higher, more preferably 0.2 or higher, still more preferably 0.3 or higher, further still more preferably 0.5 or higher, and further still more preferably 1.0 or higher from the viewpoint of exhibiting high hair dyeability on healthy hair and damaged hair as well and also dry hair and wet hair as well, and further, preferably 30 or lower, more preferably 15 or lower, still more preferably 10 or lower, further still more preferably 5 or lower, and further still more preferably 3 or lower from the similar viewpoint.

The mass ratio of the component (B) to the total of the component (A) and the component (C), (B)/[(A)+(C)], in the hair dye composition of the present invention is, from the viewpoint of exhibiting high hair dyeability on healthy hair and damaged hair as well and also dry hair and wet hair as well, preferably 1 or higher, more preferably 1.5 or higher, and still more preferably 2.0 or higher, and from the similar viewpoint, preferably 5 or lower, more preferably 4 or lower, and still more preferably 3 or lower.

<pH>

The pH (25° C.) of the hair dye composition of the present invention is 8.5 to 12 from the viewpoint of excellent hair dyeing effect and suppression of skin irritation, and preferably 9 or higher from the viewpoint of excellent hair dyeing effect, and further, preferably 11.5 or lower, and more preferably 11 or lower from the viewpoint of suppression of skin irritation. Further when the hair dye composition of the present invention is a two-part type or a three-part type, the pH (25° C.) thereof when the first part and the second part or the first part, the second part and the third part are mixed is in the above range; and it is preferable that the pH (25° C.) of the first part be 8 to 12 and the pH (25° C.) of the second part be 2 to 5. The pH adjusting agents include, in addition to an alkali agent, inorganic acids such as hydrochloric acid and phosphoric acid, organic acids such citric acid, glycolic acid and lactic acid, hydrochlorides such as monoethanolamine hydrochloride, and phosphate salts such as monopotassium dihydrogenphosphate and disodium monohydrogenphosphate. Here, in the present description, the pH of the hair dye composition is a value measured at room temperature (25° C.) by using a pH meter F-22 and a pH electrode 6367-10D, manufactured by Horiba Ltd.

[Component (D): Anionic Surfactants]

The hair dye composition of the present invention can comprise an anionic surfactant.

The component (D) includes anionic surfactants having a sulfone group, a sulfate group, a carboxyl group or a phosphate group. The component (D) specifically includes alkylbenzenesulfonate salts, alkyl or alkenyl ether sulfate salts, alkyl or alkenyl sulfate salts, olefin sulfonate salts, alkane sulfonate salts, saturated or unsaturated fatty acid salts, alkyl or alkenyl ether carboxylate salts, α-sulfofatty acid salts, N-acylamino acids, phosphate mono- or diesters and sulfosuccinate esters. Counter ions of the anionic groups of these anionic surfactants include alkali metal ions such as a sodium ion and a potassium ion; alkaline earth metal ions such as a calcium ion and a magnesium ion; an ammonium ion; and alkanolamines (for example, monoethanolamine, diethanolamine, triethanolamine and triisopropanolamine) having 2 or 3 carbon atoms and having 1 to 3 alkanol groups.

Among these components (D), an alkyl ether sulfate salt represented by the following formula (7) is preferable from the viewpoint of exhibiting high hair dyeability on healthy hair and damaged hair as well and also dry hair and wet hair as well.

$$R^6-O-(CH_2CH_2O)_u-[CH_2CH(CH_3)O]_v-SO_3M \qquad (7)$$

wherein $R^6$ denotes a hydrocarbon having 8 to 25 carbon atoms; u denotes an average addition molar number of 0 to 50; v denotes an average addition molar number of 0 to 50; and M denotes an alkali metal or $NH_4$.

The content of the (D) component in the hair dye composition is preferably 0.01 mass % or higher, more preferably 0.1 mass % or higher, and still more preferably 0.3 mass % or higher from the viewpoint of dissolving the dye, and preferably 20 mass % or lower, more preferably 10 mass % or lower, still more preferably 5 mass % or lower, further still more preferably 3 mass % or lower, further still more preferably 2.0 mass % or lower, and further still more preferably 1.5 mass % or lower from the viewpoint of exhibiting high hair dyeability on healthy hair and damaged hair as well and also dry hair and wet hair as well.

[Component (E): Nonionic Surfactants]

The hair dye composition of the present invention can comprise a nonionic surfactant.

The component (E) includes nonionic surfactants having an ether group, an ester group, an amine oxide group or an amido group. The component (E) specifically includes polyoxyalkylene alkyl ether, polyoxyalkylene alkenyl ether, higher fatty acid sucrose esters, polyglycerine fatty acid esters, higher fatty acid mono- or diethanolamide, polyoxyethylene-hardened castor oils, polyoxyethylene sorbitan fatty acid esters, polyoxyethylene sorbitol fatty acid esters, alkyl saccharides, alkylamine oxides, and alkylamidoamine oxides. Among these, from the viewpoint of exhibiting high hair dyeability on healthy hair and damaged hair as well and also dry hair and wet hair as well, preferable are polyoxyalkylene alkyl ethers, polyoxyethylene-hardened castor oils and alkyl saccharides, and more preferable are polyoxyethylene alkyl (12 to 14) ethers and alkyl polyglucosides.

Among these components (E), from the viewpoint of exhibiting high hair dyeability on healthy hair and damaged hair as well and also dry hair and wet hair as well, a polyoxyalkylene alkyl ether represented by the following formula (8) is preferable.

$$R^7—O-(AO)_w—H \qquad (8)$$

wherein $R^7$ denotes a straight-chain or branched-chain saturated or unsaturated hydrocarbon having 8 to 22 carbon atoms; A denotes an alkylene group having 2 to 4 carbon atoms; and w denotes a number of from 1 to 100 as an average value.

The content of the component (E) in the hair dye composition is preferably 0.01 mass % or higher, more preferably 0.1 mass % or higher, and still more preferably 0.3 mass % or higher from the viewpoint of dissolving the dye, and preferably 20 mass % or lower, more preferably 10 mass % or lower, still more preferably 5 mass % or lower, further still more preferably 3 mass or lower, further still more preferably 2.0 mass % or lower, and further still more preferably 1.5 mass % or lower from the viewpoint of exhibiting high hair dyeability on healthy hair and damaged hair as well and also dry hair and wet hair as well.

The mass ratio of the component (D) to the component (E), (D)/(E), in the hair dye composition of the present invention is preferably 0.5 or higher, and more preferably 0.8 or higher from the viewpoint of the blending stability, and from the viewpoint of exhibiting high hair dyeability on healthy hair and damaged hair as well and also dry hair and wet hair as well, preferably 3.5 or lower, more preferably 3 or lower, and still more preferably 2 or lower.

[Other Surfactants]

The hair dye composition of the present invention can comprise a surfactant other than the anionic surfactant of the component (D) and the nonionic surfactant of the component (E). When the hair dye composition is a two-part type or a three-part type, the other surfactant may be contained in any part of the first part, the second part and the third part. As the other surfactant, either of a cationic surfactant and an amphoteric surfactant can be used.

The cationic surfactant is preferably a mono-long-chain alkyl quaternary ammonium salt or a di-long-chain alkyl quaternary ammonium salt, and specifically includes cetrimonium chloride, steartrimonium chloride, behentrimonium chloride, stearalkonium chloride, benzalkonium chloride, stearoxypropyltrimonium chloride, and dialkyl(C12-18)dimonium chlorides, and is more preferably stearyltrimonium chloride, behentrimonium chloride, stearoxypropyltrimonium chloride or a dialkyl(C12-18)dimonium chloride. Commercially available products of the cationic surfactants include Quartamin 86W, 86P Conc., 60W, E-80K and D2345P (the above, manufactured by Kao Corp.), and Nikkol CA-2580 (manufactured by Nippon Surfactant Industries Co., Ltd.).

The amphoteric surfactant includes surfactants of carbobetaine-based ones which have an alkyl group, an alkenyl group or an acyl group having 8 to 24 carbon atoms, and amidobetaine-, sulfobetaine-, hydroxysulfobetaine-, amidosulfobetaine-, phosphobetaine-, and imidazolinium-based ones; and among these, preferable are carbobetaine-based surfactants and sulfobetaine-based surfactants. Preferable amphoteric surfactants include amidopropylbetaine laurate, coconut oil fatty acid amidopropylbetaine, lauryldimethylaminoacetatic betaine, and laurylhydroxysulfobetaine.

The surfactant other than the component (D) and the component (E) can also be used concurrently in two or more; and the content thereof in the hair dye composition is preferably 0.1 mass % to 10 mass %, and from the viewpoint of the stability of the hair dye composition, more preferably 0.5 mass % or higher, and then more preferably 5 mass % or lower, still more preferably 3 mass % or lower, and further still more preferably 2 mass % or lower.

[Alkali Agent]

The hair dye composition of the present invention can comprise an alkali agent. When the hair dye composition of the present invention is a two-part type or a three-part type, the alkali agent is contained in the first part. The alkali agent includes ammonia and salts thereof, sodium hydroxide, potassium hydroxide, alkanolamines such as monoethanolamine, isopropanolamine, 2-amino-2-methylpropanol and 2-aminobutanol, and salts thereof, alkanediamine such as 1,3-propanediamine, and salts thereof, and carbonate salts such as sodium carbonate, potassium carbonate, sodium hydrogencarbonate, potassium hydrogencarbonate and guanidine carbonate.

The alkali agent may also be used concurrently in two or more; and the content thereof in the hair dye composition is preferably 0.05 mass % or higher, more preferably 0.10 mass % or higher, and still more preferably 0.2 mass % or higher from the viewpoint of a sufficient hair dyeing effect, and further, preferably 5 mass % or lower, and more preferably 4 mass % or lower from the viewpoint of reduction of hair damage and scalp irritation.

[Hydrogen Peroxide]

When the hair dye composition of the present invention is a two-part type or a three-part type, the second part can comprise hydrogen peroxide. The content of hydrogen peroxide in the hair dye composition is preferably 0.1 mass % or higher, more preferably 0.5 mass % or higher, and still more preferably 1.0 mass % or higher from the viewpoint of a sufficient hair dyeing effect, and preferably 12 mass % or lower, more preferably 9 mass % or lower, and still more preferably 6 mass % or lower from the viewpoint of reduction of hair damage and scalp irritation.

[Higher Alcohol]

The hair dye composition of the present invention preferably comprises, from the viewpoint of improvement in feel and excellent stability, a higher alcohol having 12 or more carbon atoms. When the hair dye composition is a two-part type or a three-part type, the higher alcohol may be contained in any of the first part, the second part and the third part. These have an effect of forming a structure with the surfactants and preventing their separation, and improving feel in rinsing.

The higher alcohol is, from the viewpoint of forming a structure with the surfactants and preventing their separation, and improving feel in rinsing, preferably one having 12 or more carbon atoms, and more preferably one having 16 or more carbon atoms, and then preferably one having 30 or less carbon atoms, and more preferably one having 22 or less carbon atoms, and specifically includes myristyl alcohol, cetyl alcohol, stearyl alcohol, an arachyl alcohol, behenyl alcohol, isostearyl alcohol, 2-octyldodecanol and oleyl alcohol, and mixtures thereof.

The higher alcohol can be used concurrently in two or more; and the content thereof in the hair dye composition is preferably 3 mass % or higher, and more preferably 4 mass % or higher, and then preferably 11 mass % or lower, and more preferably 9 mass % or lower from the viewpoint of the viscosity and the stability of the hair dye composition.
[Polyhydric Alcohol]

The hair dye composition of the present invention, from the viewpoint of imparting hair moisture to the hair and suppressing hair dryness, preferably further comprises a polyhydric alcohol. When the hair dye composition is a two-part type or a three-part type, the polyhydric alcohol may be contained in any part of the first part, the second part and the third part. The polyhydric alcohol includes ones having 2 to 20 carbon atoms, and specifically includes alkylene glycols such as ethylene glycol, diethylene glycol, triethylene glycol, polyethylene glycol, propylene glycol, dipropylene glycol, polypropylene glycol, 1,2-butylene glycol, 1,3-butylene glycol, pentylene glycol and hexylene glycol; glycerols such as glycerol, diglycerol and polyglycerol; sugar alcohols such as xylitol, mannitol, galactitol and sorbitol; and besides, trimethylolethane, trimethylolpropane, and pentaerythritol.

Two or more of polyhydric alcohol may be used in combination. The content thereof in the hair dye composition is preferably 0.1 mass % or higher, more preferably 0.5 mass % or higher, and still more preferably 1.0 mass % or higher from the viewpoint of imparting hair moisture to the hair and suppressing hair dryness, and further, preferably 20 mass % or lower, more preferably 15 mass % or lower, and still more preferably 10 mass % or lower from the viewpoint of exhibiting high hair dyeability on healthy hair and damaged hair as well and also dry hair and wet hair as well.
[Medium]

The hair dye composition of the present invention uses water as its medium. The content of water in the hair dye composition is preferably 10 mass % or higher, more preferably 20 mass % or higher, still more preferably 30 mass % or higher, further still more preferably 40 mass % or higher, further still more preferably 50 mass % or higher, and further still more preferably 60 mass % or higher from the viewpoint of maintaining ease of well coating and spreading the hair dye composition on wet hair, and further, preferably 95 mass % or lower, and more preferably 90 mass % or lower from the viewpoint of excellent dyeability.

The hair dye composition of the present invention, as required, further uses an organic solvent as a medium other than water. The organic solvent includes aromatic alcohols such as benzyl alcohol and benzyloxyethanol; lower alkanols such as ethanol and 2-propanol; cellosolves such as ethyl cellosolve, butyl cellosolve and benzyl cellosolve; and carbitols such as ethyl carbitol and butyl carbitol.
[Forms of the Composition]

The hair dye composition of the present invention can be used as various types of dyes of a one-part type, a two-part type and a three-part type. The one-part type hair dye composition is composed of a single part comprising the components (A) to (C). It is preferable that the two-part type hair dye composition be composed of a first part containing the component (A) and the alkali agent, and a second part containing hydrogen peroxide. It is preferable that the three-part type hair dye composition be composed of a first part containing the alkali agent, a second part containing hydrogen peroxide and a third part containing the component (A), or a first part containing the component (A) and the alkali agent, a second part containing hydrogen peroxide and a third part containing the other components. It is preferable, in order to improve bleaching power, that the above third part containing the other components use a powdery oxidizing agent composed of a granulated material of a persulfate salt (ammonium persulfate, potassium persulfate, sodium persulfate or the like) or the like.

The hair dye composition of the present invention can be provided in a form, for example, a liquid, emulsion, cream, gel, paste or mousse form, or also in a form of aerosol. It is desirable that the viscosity of the hair dye composition in these cases be adjusted so as to hardly cause liquid sag when the composition is applied on the hair. The viscosity (25° C.) of the hair dye composition is determined as a measurement value acquired by using a B-type rotary viscometer (model: Digital Viscometer TVB-10, manufactured by Toki Sangyo Co., Ltd.) with a helical stand and a rotor T-C and after the rotor is rotated at 10 rpm for 1 minute, and is preferably from 2,000 to 200,000 mPa·s, more preferably from 4,000 to 150,000 mPa·s, even more preferably from 6,000 to 100,000 mPa·s, and further more preferably from 8,000 to 80,000 mPa·s. Here, when the hair dye composition is a two-part type or a three-part type, the measurement is carried out 3 minutes after the parts are mixed.

Further the hair dye composition of the present invention can also be used, when being applied on the hair, by discharging it from a non-aerosol-type foamer container, or by shaking it in a cup to foam and use it as foam. It is desirable that also the viscosity of the hair dye composition before being foamed in this case be adjusted so as to hardly cause liquid sag when the hair dye composition is applied as foam on the hair. The viscosity (25° C.) of the hair dye composition is determined as a measurement value acquired by using a B-type rotary viscometer (model: Digital Viscometer TV-10, manufactured by Toki Sangyo Co., Ltd.) and a rotor No. 1 and after the rotor is rotated at 30 rpm (here, when the viscosity exceeds 160 mPa·s, at 12 rpm for 1 minute), and is preferably from 1 to 800 mPa·s, more preferably from 1 to 600 mPa·s, even more preferably from 1 to 500 mPa·s, and further more preferably from 1 to 300 mPa·s. Here, the measurement is carried out in the order from the measurement at the higher rotation frequency, and completed at the time point where the measurement can be carried out without overranging of the indication of the viscometer, and no measurement at the lower rotation frequency thereafter is carried out. Here, when the hair dye composition is a two-part type or a three-part type, the measurement is carried out 3 minutes after the parts are mixed.
[Production Method of the Hair Dye Composition]

When the hair dye composition of the present invention is a one-part type, it is preferable, from the viewpoint of the stability of the hair dye composition, that the hair dye composition be prepared by mixing the component (A) and the component (C), and thereafter mixing the obtained mixture with the component (B). Further also when the hair dye composition of the present invention is a two-part type or a three-part type, and the first part contains all the components (A) to (C), it is preferable, from the viewpoint of the stability of the hair dye composition, that the first part be prepared by mixing the component (A) and the component (C), and thereafter mixing the obtained mixture with the component (B).
[Hair Dyeing Method]

In order to bleach or dye hair by using the hair dye composition of the present invention, for example, it is preferable to apply the hair dye composition of the present invention (for a two-part type, after the first part and the second part are mixed just before use; and for a three-part type, further followed by mixing the third part) on the hair, and leaving the composition for a predetermined time, and thereafter rinsing the composition off with water and drying the hair. The application temperature to the hair is from 15 to 45° C., and the application time is preferably from 1 to 60 minutes, more preferably from 2 to 45 minutes, and even more preferably from 3 to 30 minutes.

Regarding the embodiment described hitherto, preferable aspects of the present invention will be disclosed hereinafter.

<1> A hair dye composition comprising the following components (A) to (C) and having a pH (25° C.) of 8.5 to 12.

(A) one or more dyes selected from the group consisting of the following (A-1), (A-2) and (A-3).

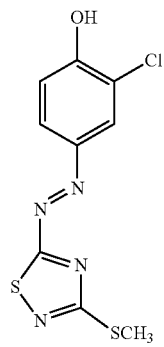

(A-1)

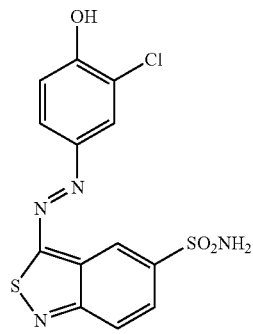

(A-2)

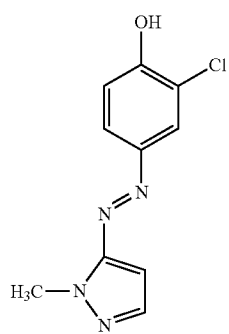

(A-3)

(B) a cationic polymer having a charge density of 3.0 meq/g or higher.

(C) an anionic polysaccharide derivative in which part of hydrogen atoms of hydroxy groups of a polysaccharide compound having a constitutional unit represented by the formula (1) is substituted by a group —$(CH_2)_m COO^-$ (m is an integer of from 1 to 5); the average degree of substitution per the constitutional unit by the group is 0.5 or higher and 2.0 or lower; and part of hydrogen atoms of the remaining hydroxy groups is optionally substituted by a straight-chain or branched-chain alkyl group and/or alkylene group having 1 to 40 carbon atoms:

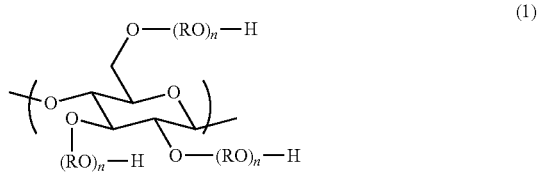

(1)

wherein each R may be identical or different and denotes a straight-chain or branched-chain alkylene group having 2 to 4 carbon atoms which is optionally substituted with a hydroxy group(s); and n denotes the number that makes an average addition molar number of RO per the constitutional unit 0 to 10.

<2> The hair dye composition according to <1>, wherein the content of the component (A) is preferably 0.0005 mass % or higher, more preferably 0.001 mass % or higher, and still more preferably 0.01 mass % or higher, and then preferably 5 mass % or lower, more preferably 3 mass % or lower, still more preferably 2.5 mass % or lower, further still more preferably 1.5 mass % or lower, and further still more preferably 1 mass % or lower.

<3> The hair dye composition according to <1> or <2>, wherein the proportion of the component (A) in the whole dye is preferably 1 mass % or higher, more preferably 5 mass % or higher, still more preferably 10 mass % or higher, further still more preferably 20 mass % or higher, further still more preferably 30 mass % or higher, and further still more preferably 40 mass % or higher.

<4> The hair dye composition according to any one of <1> to <3>, wherein the charge density of the component (B) is preferably 3.5 meq/g or higher, more preferably 4.0 meq/g or higher, and still more preferably 4.5 meq/g or higher, and then preferably 7.0 meq/g or lower, and more preferably 6.5 meq/g or lower.

<5> The hair dye composition according to any one of <1> to <4>, wherein the component (B) is preferably at least one selected from the group consisting of a polymer comprising a diallyl quaternary ammonium salt as a constitutional unit and a quaternized polyvinylimidazolium derivative.

<6> The hair dye composition according to <5>, wherein the polymer comprising a diallyl quaternary ammonium salt as a constitutional unit preferably has a skeleton represented by the following formula (2) or (3):

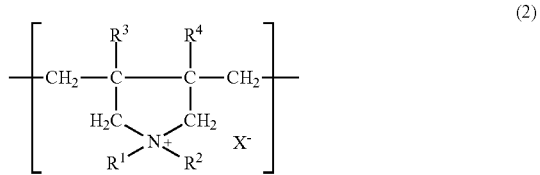

(2)

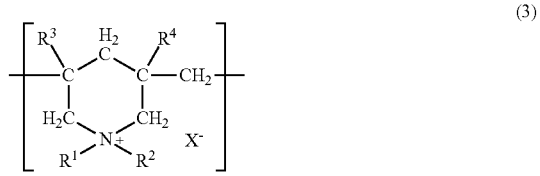

(3)

wherein $R^1$ and $R^2$ may be identical or different, and each denotes a hydrogen atom, an alkyl group having 1 to 18 carbon atoms, an aryl group (phenyl group or the like), a hydroxyalkyl group, an amidoalkyl group, a cyanoalkyl group, an alkoxyalkyl group of a carboalkoxyalkyl group;

R³ and R⁴ may be identical or different, and each denotes a hydrogen atom, an alkyl group having 1 to 3 carbon atoms, or a phenyl group; and X⁻ denotes an anion (chloride ion, bromide ion, iodide ion, sulfate anion, sulfonate anion, methylsulfate anion, phosphate anion, nitrate anion or the like).

<7> The hair dye composition according to <6>, wherein the polymer comprising a diallyl quaternary ammonium salt as a constitutional unit is preferably represented by the following formula (4) or (5):

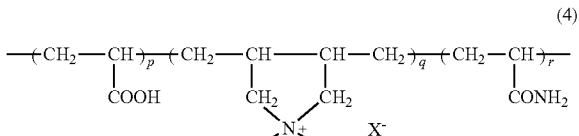

(4)

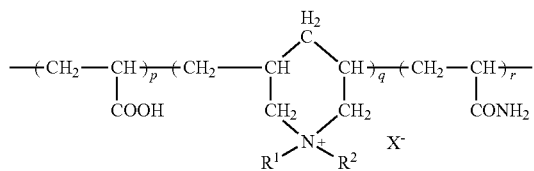

(5)

wherein R¹, R² and X⁻ denote the same meaning as in the above; and p, q and r denote molar ratios, and p+q+r=100.

<8> The hair dye composition according to <7>, wherein the polymer comprising a diallyl quaternary ammonium salt as a constitutional unit is preferably a homopolymer of a diallyl quaternary ammonium salt or a copolymer of a diallyl quaternary ammonium salt with acrylic acid.

<9> The hair dye composition according to <5>, wherein the quaternized polyvinylimidazolium derivative is preferably represented by the following formula (6):

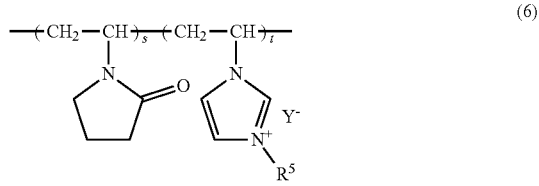

(6)

wherein R⁵ denotes an alkyl group having 1 to 3 carbon atoms; Y⁻ denotes an anion such as a chloride ion, a bromide ion, an iodide ion, a sulfate anion, a sulfonate anion, an alkylsulfate anion having 1 to 4 carbon atoms, a phosphate anion, or a nitrate anion; and s and t denote molar ratios, and s+t=100.

<10> The hair dye composition according to any one of <1> to <9>, wherein the weight-average molecular weight of the component (B) is preferably 10,000 or higher, more preferably 50,000 or higher, and even more preferably 100,000 or higher, and then preferably 3,000,000 or lower, more preferably 1,000,000 or lower, and still more preferably 800,000 or lower.

<11> The hair dye composition according to any one of <1> to <10>, wherein the content of the component (B) is preferably 0.01 mass % or higher, more preferably 0.1 mass % or higher, even more preferably 0.5 mass % or higher, and further more preferably 0.75 mass % or higher, and then preferably 20 mass % or lower, more preferably 10 mass % or lower, even more preferably 5 mass % or lower, and further more preferably 3 mass % or lower.

<12> The hair dye composition according to any one of <1> to <11>, wherein the polysaccharide compound having a constitutional unit represented by the formula (1) in the component (C) is preferably at least one selected from the group consisting of cellulose, guar gum, starch, hydroxyethyl cellulose, hydroxyethyl guar gum, hydroxyethyl starch, methyl cellulose, methyl guar gum, methyl starch, ethyl cellulose, ethyl guar gum, ethyl starch, hydroxypropyl cellulose, hydroxypropyl guar gum, hydroxypropyl starch, hydroxyethyl methyl cellulose, hydroxyethyl methyl guar gum, hydroxyethyl methyl starch, hydroxypropyl methyl cellulose, hydroxypropyl methyl guar gum, and hydroxypropyl methyl starch.

<13> The hair dye composition according to any one of <1> to <12>, wherein the component (C) is preferably a carboxymethyl cellulose.

<14> The hair dye composition according to any one of <1> to <13>, wherein the average degree of substitution per the constitutional unit by the group —(CH₂)$_m$COO⁻ in the component (C) is preferably 0.6 or higher, and more preferably 0.65 or higher, and then preferably 1.5 or lower.

<15> The hair dye composition according to any one of <1> to <14>, wherein the viscosity at 25° C. of a 1 mass % aqueous solution of the component (C) is preferably 120 mPa·s or higher, more preferably 150 mPa·s or higher, even more preferably 200 mPa·s or higher, further more preferably 800 mPa·s or higher, further still more preferably 1,000 mPa·s or higher, and further still more preferably 1,500 mPa·s or higher, and preferably 300,000 mPa·s or lower, more preferably 200,000 mPa·s or lower, even more preferably 150,000 mPa·s or lower, further more preferably 100,000 mPa·s or lower, further still more preferably 80,000 mPa·s or lower, further still more preferably 50,000 mPa·s or lower, further still more preferably 20,000 mPa·s or lower, and further still more preferably 10,000 mPa·s or lower.

<16> The hair dye composition according to any one of <1> to <15>, wherein the content of the component (C) is preferably 0.01 mass % or higher, more preferably 0.1 mass % or higher, even more preferably 0.3 mass % or higher, and further more preferably 0.5 mass % or higher, and then preferably 20 mass % or lower, more preferably 10 mass % or lower, even more preferably 5 mass % or less, further more preferably 3 mass % or lower, further still more preferably 2.0 mass % or lower, and further still more preferably 1.5 mass % or lower.

<17> The hair dye composition according to any one of <1> to <16>, wherein the mass ratio of the component (B) to the component (C), (B)/(C), is preferably 0.1 or higher, more preferably 0.2 or higher, even more preferably 0.3 or higher, further more preferably 0.5 or higher, and further still more preferably 1.0 or higher, and then preferably 30 or lower, more preferably 15 or lower, even preferably 10 or lower, further more preferably 5 or lower, and further still more preferably 3 or lower.

<18> The hair dye composition according to any one of <1> to <17>, wherein the mass ratio of the component (B) to the total of the component (A) and the component (C), (B)/[(A)+(C)], is preferably 1 or higher, more preferably 1.5 or higher, and even more preferably 2.0 or higher, and preferably 5 or lower, more preferably 4 or lower, and even more preferably 3 or lower.

<19> The hair dye composition according to any one of <1> to <18>, preferably further comprising (D) an anionic surfactant.

<20> The hair dye composition according to <19>, wherein the component (D) is preferably an alkyl ether sulfate salt represented by the following formula (7).

$$R^6\text{—O—}(CH_2CH_2O)_u\text{—}[CH_2CH(CH_3)O]_v\text{—SO}_3M \quad (7)$$

wherein $R^6$ denotes a hydrocarbon having 8 to 25 carbon atoms; u denotes an average addition molar number of from 0 to 50; v denotes an average addition molar number of from 0 to 50; and M denotes an alkali metal or $NH_4$.

<21> The hair dye composition according to <19> or <20>, wherein the content of the (D) component is preferably 0.01 mass % or higher, more preferably 0.1 mass % or higher, and even more preferably 0.3 mass % or higher, and preferably 20 mass % or lower, more preferably 10 mass % or lower, even more preferably 5 mass % or lower, further more preferably 3 mass % or lower, further still more preferably 2.0 mass % or lower, and further still more preferably 1.5 mass % or lower.

<22> The hair dye composition according to any one of <1> to <21>, preferably further comprising (E) a nonionic surfactant.

<23> The hair dye composition according to <22>, wherein the component (E) is preferably a polyoxyalkylene alkyl ether represented by the following formula (8).

$$R^7\text{—O-}(AO)_w\text{—H} \quad (8)$$

wherein $R^7$ denotes a straight-chain or branched-chain saturated or unsaturated hydrocarbon having 8 to 22 carbon atoms; A denotes an alkylene group having 2 to 4 carbon atoms; and w denotes a number of from 1 to 100 as an average value.

<24> The hair dye composition according to <22> or <23>, wherein the content of the component (E) is preferably 0.01 mass % or higher, more preferably 0.1 mass % or higher, and even more preferably 0.3 mass % or higher, and preferably 20 mass % or lower, more preferably 10 mass % or lower, even more preferably 5 mass % or lower, further more preferably 3 mass % or lower, further still more preferably 2.0 mass % or lower, and further still more preferably 1.5 mass % or lower.

<25> The hair dye composition according to any one of <22> to <24>, wherein the mass ratio of the component (D) to the component (E), (D)/(E), is preferably 0.5 or higher and 3.5 or lower, and more preferably 0.8 or higher, and then preferably 3 or lower, and more preferably 2 or lower.

<26> The hair dye composition according to any one of <1> to <25>, wherein the pH (25° C.) is preferably 9 or higher, and then preferably 11.5 or lower, and more preferably 11 or lower.

<27> A hair bleaching or dyeing method, comprising: a step of applying the hair dye composition according to any one of <1> to <26> on the hair, a step of leaving the composition preferably for from 1 to 60 minutes, more preferably for from 2 to 45 minutes and even more preferably for from 3 to 30 minutes, and a step of rinsing the composition off by using water.

EXAMPLES

Examples 1 to 3 and Comparative Examples 1 to 7

Hair dye compositions shown in Table 1 were each prepared by an ordinary method (wherein the pH (25° C.) of the each composition was adjusted to a value described in Table 1 by using phosphoric acid). A hair dyeing treatment using the each hair dye composition was carried out and the dyeability and the feel (smoothness) thereof were compared according to the following methods. Here, as damaged hair, commercially available hair (untreated healthy hair) having been subjected to a bleaching treatment was used.

[Evaluation of the hair dyeability]
—Measurement Method of $\Delta E^*$—

The color of a tress right after treatment with the hair dye composition was measured in the CIE colorimetric system (L*,a*,b*) by using a color difference meter (manufactured by Konica Minolta Sensing Co., Ltd., Chroma Meter CR-400), and the difference from the color thereof before the dyeing was determined by the following expression and taken as a dyeability $\Delta E^*$. A higher $\Delta E^*$ indicates a better dyeability.

$$\Delta E^* = \sqrt{(L_1^* - L_0^*)^2 + (a_1^* - a_0^*)^2 + (b_1^* - b_0^*)^2}.$$

In the formula, $L^*_0$, $a^*_0$ and $b^*_0$ denote values of L*, a* and b* of the tress before the dyeing, respectively; and $L^*_1$, $a^*_1$ and $b^*_1$ denote values of L*, a* and b* of the tress right after the dyeing, respectively.

<Test for Dyeability of Dried Untreated Hair>

Untreated white hair purchased from International Hair Importers & Products Inc. was made into 1 g of a tress; 0.5 g of the hair dye composition was sprayed and spread under hair kneading on the tress in a dried state over 30 seconds, and the composition was left at 30° C. for 5 minutes, thereafter rinsed off with water at about 40° C. for 30 seconds, and the hair was wiped with a towel and dried by a drier. The $\Delta E^*$ was measured from the obtained color of the tress according to the above method. The acquired measurement values are shown in Table 1.

<Test for Dyeability of Wetted Untreated Hair>

A similar tress as in the above was soaked in water at 40° C. for 30 seconds and the moisture content was adjusted to 70 mass (the moisture content per 1 g of the tress was 0.7 g). 0.25 g of the hair dye composition was sprayed and spread under hair kneading on the obtained wetted tress over 30 seconds, and the composition was left at 30° C. for 5 minutes, thereafter rinsed off with water at about 40° C. for 30 seconds, and the hair was wiped with a towel and dried by a drier. The $\Delta E^*$ was measured from the obtained color of the tress according to the above method. The acquired measurement values are shown in Table 1.

<Test for Dyeability of Dried Bleached Hair>

2 g of a mixture prepared by blending "Goldwell Bleach" and "Topchic lotion (6%)", manufactured by Goldwell Japan Co., Ltd., in a proportion of 1:1.5 in mass ratio was applied on 1 g of a similar tress as in the above in a bath ratio (the mixture:the tress)=1:2, and the mixture was left at 30° C. for 20 minutes. Then, the tress was subjected to a shampooing treatment and a rinsing treatment, and thereafter dried by a drier to thereby prepare bleached hair. 0.5 g of the hair dye composition was sprayed and spread under hair kneading on the tress of the bleached hair in the dried state over 30 sec, and the composition was left at 30° C. for 5 minutes, thereafter rinsed off with water at about 40° C. for 30 seconds, wiped with a towel and dried by a drier. The $\Delta E^*$ was measured from the obtained color of the tress according to the above method. The acquired measurement values are shown in Table 1.

<Test for Dyeability of Wetted Bleached Hair>

2 g of a mixture prepared by blending "Goldwell Bleach" and "Topchic Lotion (6%)", manufactured by Goldwell Japan Co., Ltd., in a proportion of 1:1.5 in mass ratio was applied on 1 g of a similar tress as in the above in a bath ratio (the mixture:the tress)=1:2, and the tress was left at 30° C. for 20 minutes. Then, the tress was subjected to a shampooing treatment and a rinsing treatment, and thereafter dried by a drier to thereby prepare bleached hair. The tress of the obtained bleached hair was soaked in water at 40° C. for 30 seconds and the moisture content was adjusted to at 70 mass (the moisture content per 1 g of the tress was 0.7 g). 0.25 g of the hair dye composition was sprayed and spread under hair kneading on the obtained wetted tress over 30 seconds, and the composition was left at 30° C. for 5 minutes, thereafter rinsed off with water at about 40° C. for 30 seconds, and the hair was wiped with a towel and dried by a drier. The ΔE* was measured from the obtained color of the tress according to the above method. The acquired measurement values are shown in Table 1.

[Evaluation of Feel (Smoothness)]

Untreated medium brown hair (length: 19 cm, weight of the hair: 2.2 to 3.2 g) purchased from De Meo Brothers, Inc. were subjected to a powder bleaching treatment (a mixture prepared by blending "Goldwell Bleach" and "Topchic lotion (6%)", manufactured by Goldwell Japan Co., Ltd., in a proportion of 1:1.5 in mass ratio was applied so as to become the mixture:hair=1:2, and the hair was left at 30° C. for 20 min) to thereby prepare bleached hair. The bleached hair was wetted with water and the moisture content was adjusted to 70 mass %; and thereafter, the hair dye composition was applied on the hair so as to become 25 mass of the hair, and the composition was allowed to stand still at 30° C. for 5 minutes. After the composition was rinsed off with flowing water at 40° C. for 15 seconds, the feel (smoothness) on the hair in the wet state was evaluated by researchers participating in hair care research. The evaluation used Example 1 and Comparative Examples 1 to 4 as evaluation objects, and was carried out according to the following criteria by taking Comparative Example 1 as its standard.

+2: Smoother than standard
+1: Somewhat smoother than standard
0: Same level as standard
−1: Somewhat less smooth than standard
−2: Less smooth than standard The average score (n=6) for the each treated hair is shown in Table 1.

Examples 4 to 6

Hair dye compositions shown in Table 2 were prepared, respectively, by an ordinary method (the pH (25° C.) of the each composition was adjusted to 9.8 by phosphoric acid). After the preparation of the hair dye compositions, the each composition was preserved at 25° C. and at 50° C. After three weeks, the hair dyeing treatment was carried out by using each hair dye composition, and the hair dyeability thereof was evaluated according to the above-mentioned method. The evaluation results are shown in Table 2.

TABLE 2

| | | | Example | | |
|---|---|---|---|---|---|
| Component (mass %, active amount) | | | 4 | 5 | 6 |
| (C) | carboxymethyl cellulose (*1) | | 1.88 | — | — |
| | carboxymethyl cellulose (*4) | | — | 1.88 | — |
| | carboxymethyl cellulose (*5) | | — | — | 1.88 |
| (B) | polyquaternium-22 (*2) | | 2.48 | 2.48 | 2.48 |
| (D) | sodium laureth sulfate (*6) | | 0.41 | 0.41 | 0.41 |
| (E) | Ceteth-2 (*7) | | 0.06 | 0.06 | 0.06 |
| | Ceteth-40 (*8) | | 0.35 | 0.35 | 0.35 |
| | cetyl alcohol | | 3.20 | 3.20 | 3.20 |
| | stearyl alcohol | | 1.60 | 1.60 | 1.60 |
| | perfume | | 0.25 | 0.25 | 0.25 |
| | sodium ethylenediaminetetraacetate | | 0.10 | 0.10 | 0.10 |
| | sodium chloride | | 2.00 | 2.00 | 2.00 |
| | 2-amino-2-methyl-1-propanol | | 0.80 | 0.80 | 0.80 |
| | propylene glycol | | 5.00 | 5.00 | 5.00 |
| | phosphoric acid | | *3 | *3 | *3 |
| | purified water | | balance | balance | balance |
| (A) | dye (A-1) | | 0.10 | 0.10 | 0.10 |
| | pH | | 9.8 | 9.8 | 9.8 |
| Mass Ratio | (B)/(C) | | 1.32 | 1.32 | 1.32 |
| | (B)/[(A) + (C)] | | 1.25 | 1.25 | 1.25 |
| Hair Dye- | 25° C., 3-week | dried untreated hair | 48.8 | 49.2 | 47.8 |

TABLE 1

| | | Example | | | Comparative Example | | | | | | |
|---|---|---|---|---|---|---|---|---|---|---|---|
| Component (mass %, active amount) | | 1 | 2 | 3 | 1 | 2 | 3 | 4 | 5 | 6 | 7 |
| (C) | carboxymethyl cellulose (*1) | 1.00 | 1.00 | 1.00 | — | 1.00 | 1.00 | 1.00 | 1.00 | 1.00 | 1.00 |
| (B) | polyquaternium-22 (*2) | 2.40 | 2.40 | 2.40 | 2.40 | 2.40 | 2.40 | 2.40 | 2.40 | 2.40 | 2.40 |
| | sodium chloride | 2.00 | 2.00 | 2.00 | 2.00 | 2.00 | 2.00 | 2.00 | 2.00 | 2.00 | 2.00 |
| | aminomethyl propanol | 0.80 | 0.80 | 0.80 | 0.80 | 0.80 | 0.80 | 0.80 | 0.80 | 0.80 | 0.80 |
| | propylene glycol | 5.00 | 5.00 | 5.00 | 5.00 | 5.00 | 5.00 | 5.00 | 5.00 | 5.00 | 5.00 |
| | phosphoric acid | *3 | *3 | *3 | *3 | *3 | *3 | *3 | *3 | *3 | *3 |
| | purified water | balance | balance | balance | balance | balance | balance | balance | balance | balance | balance |
| (A) | dye (A-1) | 0.10 | — | — | 0.10 | — | — | — | — | — | 0.10 |
| | dye (A-2) | — | 0.1 | — | — | — | — | — | — | — | — |
| | dye (A-3) | — | — | 0.5 | — | — | — | — | — | — | — |
| | 2-amino-6-chloro-4-nitrophenol | — | — | — | — | 0.10 | — | — | — | — | — |
| | Red No. 76 (basic dye) | — | — | — | — | — | 0.10 | — | — | — | — |
| | Red No. 33 (acid dye) | — | — | — | — | — | — | 0.10 | — | — | — |
| | Blue No. 43 (acid dye) | — | — | — | — | — | — | — | 0.10 | — | — |
| | Yellow No. 3 (acid dye) | — | — | — | — | — | — | — | — | 0.50 | — |
| | pH | 9 | 10 | 10 | 9 | 9 | 9 | 9 | 10 | 10 | 5 |
| Mass Ratio | (B)/(C) | 2.4 | 2.4 | 2.4 | — | 2.4 | 2.4 | 2.4 | 2.4 | 2.4 | 2.4 |
| | (B)/[(A) + (C)] | 2.2 | 2.2 | 1.6 | — | — | — | — | — | — | 2.2 |
| Hair Dyeability (ΔE*) | dried untreated hair | 49.5 | 30.4 | 17.7 | 48.7 | 21.4 | 9.0 | 12.4 | 4.5 | 4.3 | 10.1 |
| | wetted untreated hair | 42.7 | 26.1 | 14.6 | 34.7 | 14.4 | 14.6 | 5.9 | 4.9 | 3.5 | 15.0 |
| | dried bleached hair | 57.3 | 39.3 | 29.4 | 55.2 | 20.8 | 15.6 | 21.4 | 11.6 | 10.1 | — |
| | wetted bleached hair | 49.7 | 30.4 | 20.8 | 45.2 | 13.7 | 18.0 | 11.1 | 9.8 | 8.8 | — |
| | Smoothness | 1.2 | — | — | 0 | 1.2 | 1.2 | 1.0 | — | — | — |

*1: Sunrose F1400MC (manufactured by Nippon Paper Industries Co., Ltd., viscosity of 1 mass % aqueous solution: 8,578 mPa · s (60 rpm, 3 minutes, 25° C.); in the constitutional unit represented by the formula (1) of the polysaccharide compound as the basis, n = 0, and the average degree of substitution by a group —CH$_2$COO$^-$ is 0.7)
*2: Merquat 280 (manufactured by Lubrizol Advanced Materials, Inc., charge density: 5.0 meq/g, weight-average molecular weight: 450,000; in the formula (4), molar ratio p:q:r = 35:65:0)
*3: amount for pH adjustment TABLE 2-continued

|  |  |  | Example | | |
|---|---|---|---|---|---|
| Component (mass %, active amount) | | | 4 | 5 | 6 |
| ability (ΔE*) | Preservation | wetted untreated hair | 43.2 | 40.3 | 39.3 |
|  |  | dried bleached hair | 57.4 | 55.0 | 55.8 |
|  |  | wetted bleached hair | 46.0 | 48.7 | 49.9 |
|  | 50° C., 3-week- Preservation | dried untreated hair | 49.4 | 47.7 | 40.5 |
|  |  | wetted untreated hair | 40.1 | 39.7 | 32.4 |
|  |  | dried bleached hair | 54.7 | 53.8 | 50.9 |
|  |  | wetted bleached hair | 48.7 | 45.9 | 43.2 |

(*1) to *3: the same as in Table 1
(*4): Daicel CMC1150 (manufactured by Daicel Corp., viscosity of 1 mass % aqueous solution: 259 mPa · s (60 rpm, 3 minutes, 25° C.); in the constitutional unit represented by the formula (1) of the polysaccharide compound as the basis, n = 0, and the average degree of substitution by a group —CH$_2$COO$^-$ is 0.7)
(*5): Cellogen F-5A (manufactured by Dai-ichi Kogyo Seiyaku Co., Ltd., the viscosity of 1 mass % aqueous solution: <3 mPa · s (60 rpm, 3 minutes, 25° C.); in the constitutional unit represented by the formula (1) of the polysaccharide compound as the basis, n = 0, and the average degree of substitution by a group —CH$_2$COO$^-$ is 0.75)
(*6): Emal 270-D (manufactured by Kao Corp.; in the formula (7), R$^6$ = C$_{12}$H$_{25}$, and u = 0 and v = 2)
(*7): BRIJ C2-SO-(AP) (manufactured by Croda International plc; in the formula (8), R$^7$ = C$_{16}$H$_{33}$, A = CH$_2$CH$_2$ and w = 2)
(*8): Nikkol BC-40TX (manufactured by Nikko Chemicals Co., Ltd.; in the formula (8), R$^7$ = C$_{16}$H$_{33}$, A = CH$_2$CH$_2$ and w = 40)

The invention claimed is:

1. A hair dye composition, comprising components (A) to (C), and having a mass ratio of the component (B) to the component (C), (B)/(C), in a range of 0.1 to 30 and a pH (25° C.) of 8.5 to 12:

(A) one or more dyes selected from the group consisting of (A-1), (A-2) and (A-3):

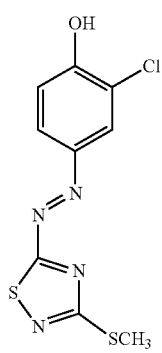

(A-1)

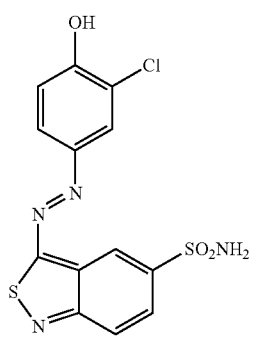

(A-2)

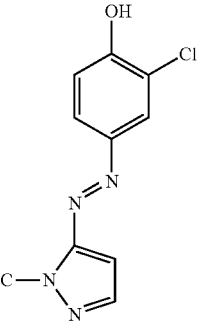

(A-3)

(B) a cationic polymer having a charge density of 3.0 meq/g or higher; and (C) an anionic polysaccharide derivative, wherein part of hydrogen atoms of hydroxy groups of a polysaccharide compound having a constitutional unit represented by the formula (1) is substituted by a group —(CH$_2$)$_m$COO$^-$, where m is an integer of from 1 to 5; an average degree of substitution per the constitutional unit by the group is 0.5 to 2.0; and part of hydrogen atoms of the remaining hydroxy groups is optionally substituted by a straight-chain or branched-chain alkyl group and/or alkylene group having 1 to 40 carbon atoms:

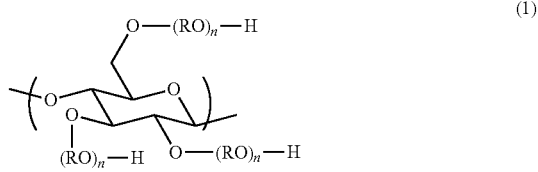

(1)

wherein each R may be identical or different and denotes a straight-chain or branched-chain alkylene group having 2 to 4 carbon atoms which is optionally substituted with a hydroxy group(s); and n denotes the number that makes an average addition molar number of RO per the constitutional unit 0 to 10.

2. The hair dye composition according to claim 1, wherein a content of the component (A) is 0.0005 mass % to 5 mass %.

3. The hair dye composition according to claim 1, wherein the component (B) is at least one selected from the group consisting of a polymer comprising a diallyl quaternary ammonium salt as a constitutional unit and a quaternized polyvinylimidazolium derivative.

4. The hair dye composition according to claim 3, wherein the polymer comprising a diallyl quaternary ammonium salt as a constitutional unit is a homopolymer of a diallyl quaternary ammonium salt or a copolymer of a diallyl quaternary ammonium salt with acrylic acid.

5. The hair dye composition according to claim 1, wherein a content of the component (B) is 0.01 mass % to 20 mass %.

6. The hair dye composition according to claim 1, wherein the polysaccharide compound having a constitutional unit represented by the formula (1) in the component (C) is at least one selected from the group consisting of cellulose, guar gum, starch, hydroxyethyl cellulose, hydroxyethyl guar gum, hydroxyethyl starch, methyl cellulose, methyl guar gum, methyl starch, ethyl cellulose, ethyl guar gum, ethyl starch, hydroxypropyl cellulose, hydroxypropyl guar gum, hydroxypropyl starch, hydroxyethyl methyl cellulose, hydroxyethyl methyl guar gum, hydroxyethyl methyl starch, hydroxypropyl methyl cellulose, hydroxypropyl methyl guar gum, and hydroxypropyl methyl starch.

7. The hair dye composition according to claim 1, wherein the component (C) is carboxymethyl cellulose.

8. The hair dye composition according to claim 1, wherein a content of the component (C) is 0.01 mass % to 20 mass %.

9. The hair dye composition according to claim 1, wherein a viscosity of the component (C) as a 1 mass % aqueous solution thereof at 25° C. is 120 mPa·s to 300,000 mPa·s.

10. The hair dye composition according to claim 1, wherein a mass ratio of the component (B) to a total of the component (A) and the component (C) in the whole composition, (B)/[(A)+(C)], is in a range of 1 to 5.

11. The hair dye composition according to claim 1, wherein the component (B) has a charge density of 7.0 meq/g or lower.

12. The hair dye composition according to claim 1, further comprising (D) an anionic surfactant.

13. The hair dye composition according to claim 12, wherein the component (D) is an alkyl ether sulfate salt represented by formula (7):

$$R^6\text{—O—}(CH_2CH_2O)_u[CH_2CH(CH_3)O]_v\text{—SO}_3M \quad (7)$$

wherein $R^6$ denotes a hydrocarbon having 8 to 25 carbon atoms; u denotes an average addition molar number of from 0 to 50; v denotes an average addition molar number of from 0 to 50; and NA denotes an alkali metal or $NH_4$.

14. The hair dye composition according to claim 1, further comprising (E) a nonionic surfactant.

15. The hair dye composition according to claim 14, wherein the component (E) is a polyoxyalkylene alkyl ether represented by formula (8):

$$R^7\text{—O-}(AO)_w\text{—H} \quad (8)$$

wherein $R^7$ denotes a straight-chain or branched-chain saturated or unsaturated hydrocarbon having 8 to 22 carbon atoms; A denotes an alkylene group having 2 to 4 carbon atoms; and w denotes the number of from 1 to 100 as an average value.

16. The hair dye composition according to claim 14, wherein a mass ratio of the component (D) to the component (E), (D)/(E), is in a range of 0.5 to 3.5.

17. A hair bleaching or dyeing method, comprising:
applying the hair dye composition according to claim 1 on the hair,
leaving the composition for from 1 to 60 minutes, and rinsing the composition off by using water.

18. The hair dye composition according to claim 1, wherein the component (B) is a polymer comprising a diallyl quaternary ammonium salt as a constitutional unit, and the polymer comprising a diallyl quaternary ammonium salt as a constitutional unit has a skeleton represented by formula (2) or (3):

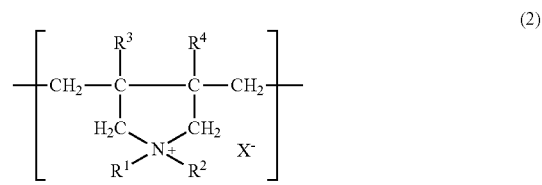

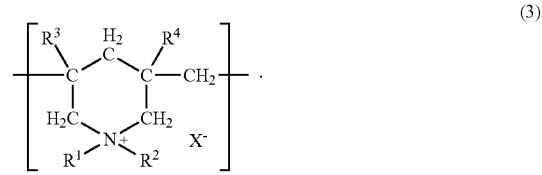

wherein $R^1$ and $R^2$ may be identical or different, and each denotes a hydrogen atom, an alkyl group having 1 to 18 carbon atoms, an aryl group, a hydroxyalkyl group, an amidoalkyl group, a cyanoalkyl group, an alkoxyalkyl group or a carboalkoxyalkyl group; $R^3$ and $R^4$ may be identical or different, and each denotes a hydrogen atom, an alkyl group having 1 to 3 carbon atoms, or a phenyl group; and $X^-$ denotes an anion.

19. The hair dye composition according to claim 1, wherein the component (B) is a polymer comprising a diallyl quaternary ammonium salt as a constitutional unit, and the polymer comprising a diallyl quaternary ammonium salt as a constitutional unit has a skeleton represented by formula (4) or (5):

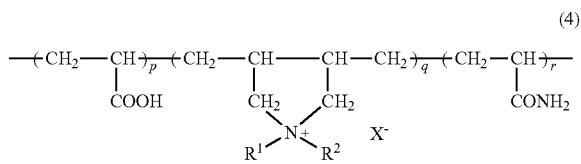

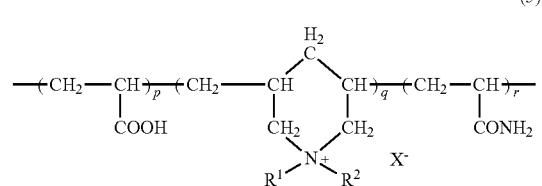

wherein $R^1$ and $R^2$ may be identical or different, and each denotes a hydrogen atom, an alkyl group having 1 to 18 carbon atoms, an aryl group, a hydroxyalkyl group, an amidoalkyl group, a cyanoalkyl group, an alkoxyalkyl group or a carboalkoxyalkyl group; $X^-$ denotes an anion; and p, q and r denote molar ratios wherein p+q+r=100.

* * * * *